United States Patent
Pakulski et al.

(10) Patent No.: US 9,719,007 B2
(45) Date of Patent: Aug. 1, 2017

(54) ALKYLATED POLYETHERAMINES AS CLAY STABILIZING AGENTS

(71) Applicant: Huntsman Petrochemical LLC, The Woodlands, TX (US)

(72) Inventors: Marek K Pakulski, The Woodlands, TX (US); Matthew W. Forkner, Spring, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 0 days.

(21) Appl. No.: 14/421,462

(22) PCT Filed: Nov. 4, 2013

(86) PCT No.: PCT/US2013/068261
§ 371 (c)(1),
(2) Date: Feb. 13, 2015

(87) PCT Pub. No.: WO2014/074443
PCT Pub. Date: May 15, 2014

(65) Prior Publication Data
US 2015/0299554 A1    Oct. 22, 2015

Related U.S. Application Data

(60) Provisional application No. 61/725,204, filed on Nov. 12, 2012.

(51) Int. Cl.
| | |
|---|---|
| C09K 8/04 | (2006.01) |
| C09K 8/22 | (2006.01) |
| C09K 8/58 | (2006.01) |
| C09K 8/52 | (2006.01) |
| C09K 8/68 | (2006.01) |
| C09K 8/74 | (2006.01) |
| C09K 8/86 | (2006.01) |
| E21B 43/16 | (2006.01) |

(52) U.S. Cl.
CPC .......... *C09K 8/22* (2013.01); *C09K 8/04* (2013.01); *C09K 8/52* (2013.01); *C09K 8/58* (2013.01); *C09K 8/68* (2013.01); *C09K 8/74* (2013.01); *C09K 8/86* (2013.01); *E21B 43/16* (2013.01); *C09K 2208/12* (2013.01); *C09K 2208/22* (2013.01)

(58) Field of Classification Search
None
See application file for complete search history.

(56) References Cited

U.S. PATENT DOCUMENTS

| | | | |
|---|---|---|---|
| 2,947,360 | A | 8/1960 | Bernard |
| 4,927,912 | A | 5/1990 | Speranza et al. |
| 6,247,543 | B1 | 6/2001 | Patel et al. |
| 7,250,390 | B2 | 7/2007 | Patel et al. |
| 8,157,010 | B2 | 4/2012 | Murphy et al. |
| 2003/0148892 | A1 | 8/2003 | Klein et al. |
| 2005/0049150 | A1 | 3/2005 | Patel et al. |
| 2007/0208156 | A1* | 9/2007 | Posey ............... C08G 18/3821 528/44 |
| 2010/0087566 | A1* | 4/2010 | Ballard ............... C09K 3/22 523/130 |
| 2011/0061866 | A1 | 3/2011 | Patel et al. |
| 2012/0148858 | A1* | 6/2012 | Wu ................ C09D 15/00 428/537.1 |

FOREIGN PATENT DOCUMENTS

| | | |
|---|---|---|
| CN | 102391842 A | 3/2012 |
| CN | 102676148 A | 9/2012 |
| WO | 2011/083182 A | 7/2011 |

OTHER PUBLICATIONS

Jacaab LLC; Jacaab-Ethomeen C/15 Material Safety Data Sheet; May 26, 2005.
Lei Wang et al. "Effect of poly(oxypropylene)diamine adsorption on hydration and dispersion of montmorillonite particles in aqueous solution", Colloids and Surfaces. A, Physicochemical and Engineering Aspects, vol. 381, No. 1-3, May 1, 2011, pp. 41-47.
Yannan Cui et al. "Adsorption of Polyetheramines on Montmorillonite at High pH", Langmuir, vol. 26, No. 22, Nov. 16, 2010, pp. 17210-17217.
Chinese Office Action dated Dec. 22, 2016 regarding CN Application 201380042778.2 "Alkylated Polyetheramines as Clay Stabilizing Agents", Applicant: Huntsman Petrochemcial LLC.

* cited by examiner

*Primary Examiner* — Alicia Bland
(74) *Attorney, Agent, or Firm* — Huntsman International LLC

(57) ABSTRACT

The present disclosure provides water-based well treatment fluids for use in treating subterranean formations to prevent swelling and/or migration of fines. The water-based well treatment fluid contains an aqueous continuous phase, a clay stabilizing agent consisting of an alkylated polyetheramine and a weighting material. In addition to inhibiting swelling and/or migration, the water-based well treatment fluids are thermally stable, are toxicologically safe, and have exceptional handling properties.

12 Claims, No Drawings

ALKYLATED POLYETHERAMINES AS CLAY STABILIZING AGENTS

CROSS-REFERENCE TO RELATED APPLICATIONS

This application is the National Phase of International Application PCT/US2013/068261 filed Nov. 4, 2013 which designated the U.S. and which claims priority to U.S. App. Ser. No. 61/725,204 filed Nov. 12, 2012. The noted applications are incorporated herein by reference.

STATEMENT REGARDING FEDERALLY SPONSORED RESEARCH OR DEVELOPMENT

Not Applicable.

FIELD OF THE INVENTION

The present disclosure relates generally to well treatment fluids and their use. More specifically, the present disclosure relates to alkylated polyetheramines as clay stabilizing agents in well treatment fluids and methods of using the same.

BACKGROUND OF THE INVENTION

The production of hydrocarbons from subterranean formations is often effected by the presence of clays and other fines which can migrate and plug off or restrict the flow of the hydrocarbon product. The migration of fines in a subterranean formation is often the result of clay swelling, salt dissolution, and/or the disturbance of fines by the introduction of fluids that are foreign to the formation. Typically, such foreign fluids (e.g. drilling fluid, fracturing fluid or stabilizing fluid) are introduced into the formation for the purpose of completing and/or treating the formation to stimulate production of hydrocarbons by, for example, drilling, fracturing, acidizing, or stabilizing the well.

Attempts to diminish the damaging effects caused by introduction of the foreign fluid and the swelling and migration of the components of the formations has included the addition of one or more various shale hydration inhibitors and/or stabilizing agents into such foreign fluids. These work on the principle of the substitution of a cationic species in the clay lattice for a sodium ion. The cationic species is generally selected such that its radius of hydration is less than that of the sodium ion. It is believed that the molecules of the shale hydration inhibitors and stabilizing agents compete with molecules of water for reactive sites. Thus, the possibility of swelling and migration is minimized upon their contact with the formation. As a result, the probability of disintegration of formation is diminished and swelling is inhibited.

Potassium chloride has been widely used as a shale inhibitor/clay stabilizer. In stimulation methods, potassium chloride has often been used as a preflush and/or added to aqueous stimulation methods in order to convert the clay to a less swellable form. While such salts diminish the reduction of formation permeability, they are often detrimental to the performance of other constituents of the foreign fluid. For example, high concentration of such salts is typically required for stabilization of clay (typically 6%). Such salts further produce high chloride levels which are environmentally unacceptable. Other known shale hydration inhibitors/clay stabilizing agents, which have been used include, for example:

WO 98/55733, which discloses the use of at least one organic amine selected from a primary diamine with a chain length of less than 8 carbon atoms and a primary alkyl amine with a chain length of less than 4 carbon atoms:

WO 05/058986, which teaches the use of an amine salt of an imide of a maleic anhydride polymer;

WO 06/013595, which discloses adducts of carboxymethyl cellulose and an organic amine as solid shale inhibitors;

WO 06/013597, which teaches the use of 0.2-5% by wt. of 1,2-diaminocyclohexane to inhibit the swelling of clay;

WO 06/136031, which teaches the use of amine salts having different molecular weights so as to be able to transport into micropore, mesospore and macrospores in the formation and effect cationic exchange therein;

WO 10/040223, which discloses the use of bis-surfactant diamine compounds to reduce clay swelling while drilling is carried out;

U.S. Pat. No. 4,719,021, which teaches incorporating a polyvalent metal/guanidine complex into a drilling fluid to stabilize colloidal clay;

U.S. Pat. No. 4,988,450, which discloses polymers of vinyl acetate combined with potassium salts as an additive for aqueous mud for improving wellbore stability;

U.S. Pat. No. 6,706,667, which discloses a shale-stabilizing additive for water-based drilling fluids including a polymer based on an olefinically unsaturated hydrocarbon with alkylene oxide based side chains;

U.S. Pat. Nos. 6,831,043 and 6,857,485, which teach the use of polyether amines as shale hydration inhibition agents;

U.S. Pat. No. 7,192,907, which discloses quaternary compounds as shale encapsulating agents to at least partially inhibit swelling and aid in the action of conventional shale inhibitors;

U.S. Pat. No. 7,514,392, which teaches the use of bis-cyclohexylamine derivatives as shale hydration inhibitors;

U.S. Pat. No. 7,939,473, which discloses monoquaternary hydroxyalkylalkylamines or poly(trihydroxyalklyalkylquaternary amines) as additives for reducing the swelling of clay in wells;

U.S. Pat. No. 8,026,198, which teaches the use of propylamine derivatives, hydrogenated poly (propyleneimine) dendrimers and polyamine twin dendrimers as shale hydration inhibitors;

U.S. Pat. No. 8,220,565, which teaches the use of a guanidyl copolymer to stabilize a subterranean formation; and U.S. Pat. No. 8,252,728, which discloses polymers containing hydroxylated structural units which are useful for inhibiting swelling of clays.

There is a continuing need for the development of shale hydration inhibitors/clay stabilizing agents which are substantially odor free, pose little threat to the environment by eliminating substantially all chlorides, and are as at least as effective as the most effective prior art hydration inhibitor/stabilizing agents.

SUMMARY OF THE INVENTION

The present disclosure provides a water-based well treatment fluid which is used in downhole fluid introduced into a subterranean formation containing clay subterranean materials that have a tendency to exhibit swelling and/or migration upon exposure to water. The well treatment fluid contains an aqueous continuous phase, a clay stabilizing agent consisting of an alkylated polyetheramine and a weighting material.

In another aspect, the present disclosure provides a method of inhibiting swelling and/or migration of clay subterranean materials encountered during the drilling of a subterranean formation. The method includes circulating in the subterranean formation a water-based well treatment fluid containing an aqueous continuous phase, a clay stabilizing agent consisting of an alkylated polyetheramine and a weighting material.

DETAILED DESCRIPTION OF THE INVENTION

As used herein, the term "comprising" and derivatives thereof are not intended to exclude the presence of any additional component, step or procedure, whether or not the same is disclosed herein. In order to avoid any doubt, all compositions claimed herein through use of the term "comprising" may include any additional additive or compound, unless stated to the contrary. In contrast, the term, "consisting essentially of" if appearing herein, excludes from the scope of any succeeding recitation any other component, step or procedure, excepting those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or more than one (i.e. to at least one) of the grammatical object of the article. By way of example, "an alkylated polyetheramine" means one alkylated polyetheramine or more than one alkylated polyetheramine.

The phrases "in one embodiment", "according to one embodiment" and the like generally mean the particular feature, structure, or characteristic following the phrase is included in at least one embodiment of the present invention, and may be included in more than one embodiment of the present invention. Importantly, such phases do not necessarily refer to the same embodiment.

If the specification states a component or feature "may", "can", "could", or "might" be included or have a characteristic, that particular component or feature is not required to be included or have the characteristic.

The phrase "subterranean formation" encompasses both areas below exposed earth and areas below earth covered by water, such as an ocean or fresh water. The term "clay subterranean materials" includes sand and/or clays which swell, disperse, disintegrate or otherwise become disrupted, thereby demonstrating an increase in bulk volume, in the presence of foreign aqueous well treatment fluids, such as drilling fluids, stimulation fluids, gravel packing fluids, etc. The term also includes those sand and/or clays which disperse, disintegrate or otherwise become disrupted without actual swelling. For example, clays which, in the presence of foreign aqueous well treatment fluids, expand and may be disrupted by becoming unconsolidated, thereby producing particles that migrate into a borehole shall also be included by the term.

The clay stabilizing agent consisting of an alkylated polyetheramine as defined herein can be used as a total potassium chloride substitute when potassium chloride is used as a clay stabilizing agent. In addition, the clay stabilizing agent consisting of an alkylated polyetheramine can be used in water-based well treatment fluids and methods where potassium chloride or other inorganic salts have not been traditionally used. In some embodiments, the clay stabilizing agent consists essentially of an alkylated polyetheramine and can be used in water-based well treatment fluids in conjunction with potassium chloride. When combined with an aqueous continuous phase and a weighting material to render a water-based well treatment fluid, the clay stabilizing agent consisting of an alkylated polyetheramine is capable of reducing or substantially eliminating damage to a subterranean formation caused by swellable and/or migrating clay subterranean materials. The presence of the clay stabilizing agent consisting of an alkylated polyetheramine eliminates or reduces the tendency of the clay subterranean materials to swell and/or disintegrate/migrate upon contact with the water-based well treatment fluid.

Such inhibition and/or migration may be temporary or substantially permanent depending on the quantity of water-based well treatment fluid used to treat the subterranean formation. Thus, another advantage of using the disclosed clay stabilizing agent consisting of an alkylated polyetheramine is evidenced by its ability to provide permanent clay stabilization. Temporary clay stabilizers are materials that protect the subterranean formation only during treatment of the formation with the water-based well treatment fluid. Migration of natural fluids over the subterranean formation over time displaces foreign cations, thereby reverting the clay back to its natural swelling form. In contrast, permanent clay stabilizers minimize such swelling when the clays are exposed to natural fluids over time without the need of continued addition of the water-based well treatment fluid.

In addition to inhibiting swelling and/or migration, the clay stabilizing agents consisting of an alkylated polyetheramine disclosed herein also achieve other benefits. For instance, the clay stabilizing agents consisting of an alkylated polyetheramine are thermally stable, are toxicologically safer, and have better handling properties. Therefore, the clay stabilizing agents consisting of an alkylated polyetheramine may be broadly utilized in land based drilling operations as well as offshore drilling operations.

Thus, according to one embodiment, a water-based well treatment fluid is provided comprising an aqueous continuous phase, a clay stabilizing agent consisting of an alkylated polyetheramine and a weighting material.

The water-based well treatment fluid may be any fluid capable of delivering the clay stabilizing agent consisting of an alkylated polyetheramine into a subterranean formation. Thus, in one embodiment, the water-based well treatment fluid is a drilling fluid, a drill-in-fluid, a stimulation fluid, a fracturing fluid, an acidizing fluid, a remedial fluid, a well reworking fluid or a gravel pack fluid.

According to another embodiment, the aqueous continuous phase is any water based fluid phase that is compatible with the formulation of a well treatment fluid and is also compatible with the clay stabilizing agents disclosed herein. In one embodiment, the aqueous continuous phase is selected from fresh water, sea water, brine, a mixture of water and a water soluble organic compound and mixtures thereof. The amount of the aqueous continuous phase should be sufficient to form a water-based well treatment fluid. In one embodiment, the amount of aqueous continuous phase may range from nearly 100% of the water-based well treatment fluid by volume to less than 30% of the water-based well treatment fluid by volume. In another embodiment, the amount of the aqueous based continuous phase is from about 95% by volume to about 30% by volume of the water-based well treatment fluid. In still another embodiment, the amount of the aqueous based continuous phase is from about 90% by volume to about 40% by volume of the water-based well treatment fluid.

As discussed above, the water-based well treatment fluid also includes a clay stabilizing agent consisting of an alkylated polyetheramine. In one embodiment, the alkylated polyetheramine is a compound having the formula (I):

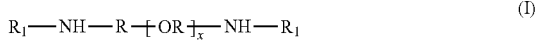

(I)

wherein R is $C_2H_4$ or $CH(CH_3)CH_2$,
$R_1$ is a straight chain or branched $C_1$ to $C_6$ alkyl group, and x is an integer from 1 to 3. In one embodiment, R is $C_2H_4$, and $R_1$ is a methyl group, ethyl group, n iso-propyl group, n-propyl group, n-iso-butyl or n-butyl group. According to another embodiment, R is $C_2H_4$, and $R_1$ is an ethyl group, n iso-propyl group or n-propyl group. In one illustrative embodiment of the present disclosure, the clay stabilizing agent is a compound having the formula (II) or a compound having the formula (III) or a compound having the formula (IV):

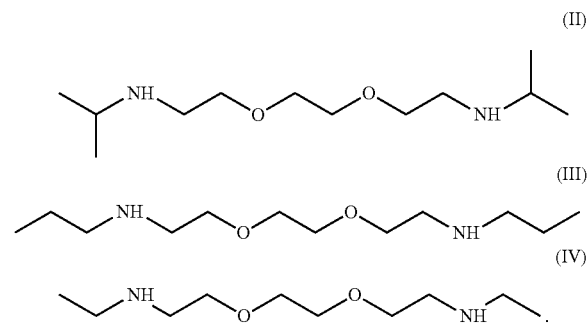

In another illustrative embodiment, of the present disclosure, the clay stabilizing agent is a compound having the formula (II) or a compound having the formula (IV):

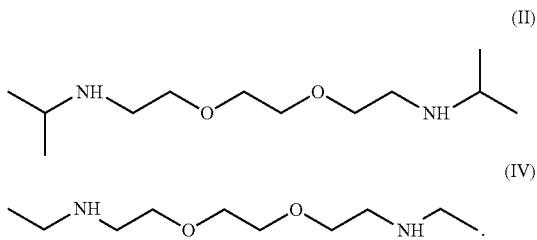

Generally, the clay stabilizing agent is present in the water-based well treatment fluid in an amount sufficient to reduce either or both of surface hydration based swelling and/or osmotic based swelling of clay subterranean materials. The exact amount of the clay stabilizing agent present in a particular water-based well treatment fluid may be determined by a trial and error method of testing the combination of water-based well treatment fluid and clay formation encountered. In one embodiment, the amount of clay stabilizing agent of the present disclosure used in the water-based well treatment fluids ranges from about 1 to about 20 pounds per barrel (lbs/bbl or ppb) of water-based well treatment fluid. In another embodiment, the amount of clay stabilizing agent present in the water-based well treatment fluid ranges from about 2 to about 18 ppb of water-based well treatment fluid. In still another embodiment, the amount of clay stabilizing agent present in the water-based well treatment fluid ranges from about 0.05% to about 0.5% by volume of the water-based well treatment fluid.

The water-based well treatment fluid also contains a weighting material. The weighting material increases the density of the fluid in order to prevent kick-backs and blow-outs. Suitable weighting materials include any type of weighting material that is in solid form, particulate form, suspended in solution, or dissolved in the aqueous continuous phase. In one embodiment, the weighting material is barium sulfate, barite, hematite, iron oxide, calcium carbonate, magnesium carbonate, an organic salt, an inorganic salt or mixtures thereof. The amount of weighting material present in the water-based well treatment fluid is an amount effective to prevent kick-backs and blow-outs, which amount changes according to the nature of the formation under treatment operations. In one particular embodiment, the weighting material is included in the water-based well treatment fluid at a level of less than 800 ppb, for example, from about 5 ppb to about 750 ppb or from about 10 ppb to about 700 ppb of water-based well treatment fluid.

In another embodiment, the water-based well treatment fluid optionally contains one or more conventional additives. Examples of such additives include, but are not limited to, gelling materials, thinners, fluid loss control agents, encapsulating agents, bactericides, gel breakers, foaming agents, stabilizers, lubricants, penetration rate enhancers, defoamers, corrosion inhibitors, lost circulation fluids, anti-bit balling agents, neutralizing agents, pH buffering agents, surfactants, proppants, and sand for gravel packing.

Examples of gelling materials include, but are not limited to, bentonite, sepiolite clay, attapulgite clay, anionic high-molecular weight polymers and biopolymers.

Examples of thinners include, but are not limited to, lignosulfates, modified lignosulfates, polyphosphates, tannins, and low molecular weight polyacrylates.

Examples of fluid loss control agents include, but are not limited to, synthetic organic polymers, biopolymers and mixtures thereof, modified lignite polymers, modified starches and modified celluloses.

Examples of encapsulating agents include, but are not limited to, synthetic materials, organic materials, inorganic materials, biopolymers or mixtures thereof. The encapsulating agent may be anionic, cationic or non-ionic in nature.

The clay stabilizing agent of the present disclosure and weighting material and optional additives may be admixed with the aqueous continuous phase to form the water-based well treatment fluid. Thus, in another embodiment, there is provided a process of making a water-based well treatment fluid comprising admixing a clay stabilizing agent consisting of an alkylated polyetheramine, a weighting material and optional additives with an aqueous continuous phase.

In another embodiment, there is provided a method of inhibiting the swelling and/or migration of clay subterranean materials encountered during the drilling of a subterranean formation. The method includes circulating in the subterranean formation a water-based well treatment fluid containing an aqueous continuous phase, a clay stabilizing agent consisting of an alkylated polyetheramine and a weighting material. In still another embodiment, there is provided a method for stabilizing a subterranean formation including the steps of contacting the subterranean formation with the water-based well treatment fluid of the present disclosure. Contacting the subterranean formation may be accomplished, for example, by providing the water-based well treatment fluid disclosed herein to the subterranean formation before, during or after hydraulic fracturing or drilling.

Clay subterranean materials which may be effectively treated with the water-based well treatment fluid may be of varying shapes, such as minute, plate-like, tube-like and/or fiber-like particles having an extremely large surface area. Examples include clay minerals of the montmorillonite (smectite) group such as montmorillonite, saponite, nontronite, hectorite and sauconite, the kaolin group such as kaolinite, nacrite, dickite, and halloysite, the hydrousmica group such as hydrobiotite, gluaconite, illite and bramallite, the chlorite group such as chlorite and chamosite, clay minerals not belonging to the above group such as vermiculite, attapulgite and sepiolite and mixed-layer varieties of such clay minerals and groups. Other mineral components may be further associated with the clay.

In another embodiment, the materials and method of inhibiting swelling and/or migration of clay subterranean materials and stabilizing the subterranean formation can be provided as a kit that includes a sufficient amount of the clay stabilizing agent, weighting material and optional additives for on-site admixture with the aqueous continuous phase.

The result of stabilization of the subterranean formation with the water-based well treatment fluid described herein is that clay subterranean material particulates loosened from the subterranean formation by the process of removing a hydrocarbon product have reduced swell, have reduced subterranean migration, do not reduce the flow of the hydrocarbon product, and/or do not contaminate the hydrocarbon product. Without the water-based well treatment fluid, the clay subterranean materials can swell and/or migrate to inhibit or contaminate the hydrocarbon production. The stabilization effect can be measured by comparing wells with and without the water-based well treatment fluid or comparing the flow rate of fluids (e.g. oil, water or natural gas) through samples from the subterranean formation with and without the water-based well treatment fluid.

Subterranean formations can be stabilized by contacting them with the water-based well treatment fluid. In one embodiment, clay subterranean materials swelling and/or fines migration can be reduced by contacting the subterranean formation with a water-based well treatment fluid comprising an aqueous continuous phase, a clay stabilizing agent consisting of an alkylated polyetheramine, a weighting material and optional additives.

In another embodiment, a previously hydraulically fractured subterranean formation can be restabilized by contacting the hydraulically fractured subterranean formation with a water-based well treatment fluid comprising an aqueous continuous phase, a clay stabilizing agent consisting of an alkylated polyetheramine, a weighting material and optional additives. The hydraulically fractured subterranean formation can be a hydraulically fractured subterranean formation, for example, that from which hydrocarbons have been extracted. Preferably, the hydraulically fractured subterranean formation is a formation having a mineral content that is predominantly clay, shale, sand, and/or a mixture thereof.

In still another embodiment, the water-based well treatment fluid can be used in a method of flushing a bore hole during drilling. The method includes applying the water-based well treatment fluid to a drill head during drilling of a subterranean formation.

In yet another embodiment, there is provided a method of extracting oil from an oil containing subterranean formation by providing through a first borehole, a pressurized water-based well treatment fluid of the present disclosure and recovering oil from the subterranean formation through a second borehole. Preferably, the subterranean formation was previously hydraulically fractured and oil was previously extracted.

EXAMPLES

The following examples are provided to illustrate the invention, but are intended not to limit the scope thereof.

Example 1

Capillary Suction Time (CST) tests were measured as a determination of the relative flow capacity of a slurry of ground formation rock used to form an artificial core. Wyoming bentonite clay was ground and 5% by weight of the ground clay was added to 95% by weight of silica flour to form a core sample. 4 grams of the core sample was then placed in 40 ml of a test fluid (the test fluid comprising the clay stabilizing agent and water) and stirred on a magnetic stirrer for at least 30 minutes. 5 ml of this slurry was then placed into a metal funnel containing filter paper of the CST instrument and the time needed for the slurry to travel down a certain distance was recorded.

Here, the data obtained from the CST test is reported as a % Change obtained from the equation:

$$((CST_{sample}/CST_{blank})-1)\times 100 = \_\% \text{ Change}$$

where $CST_{blank}$ is the CST time for the test fluid (a 5% by weight of KCl dissolved in water) to flow the required distance without a core sample present. Four clay stabilizing agents were tested: Example 1=2-propanamine, NN'-[1,2-ethanediylbis(oxy-2,1-ethanediyl)]bis- (Structure II); Example 2=ethanamine, NN'-[1,2-ethanediylbis(oxy-2,1-ethanediyl)]bis-, (Structure IV); Comparative Example 3 JEFFAMINE® D-230 polyetheramine (Structure I R=CH(CH$_3$)CH$_2$, R$^1$=H available from Huntsman Petrochemical LLC) and Comparative Example 4=JEFFAMINE® SD-231 polyetheramine (Structure 1 R=CH(CH$_3$)CH$_2$, R$^1$=i-C$_3$H$_7$ available from Huntsman Petrochemical LLC). In some of the test fluids, the clay stabilizing was first neutralized by contacting 20 g of the clay stabilizing agent with either 0.5, 0.6 or 2 moles of glacial acetic acid or concentrated HCl (37%). They are reported below as neat amine or salt concentration:

TABLE 1

| Clay Stabilizing Agent | Concentration (% by wt. in water) | 30 Minute Contact Time (sec) | % Change |
|---|---|---|---|
| None (100% Water) | 0 | 237 | — |
| KCl (Blank) | 5 | 17.6 | — |
| Example 1 Neat Amine | 0.1 | 24 | 36.4 |
| Example 1 Neat Amine | 0.25 | 21.2 | 20.5 |
| Example 1 Neat Amine | 0.5 | 23.3 | 32.4 |
| Example 2 Neat Amine | 0.1 | 16.6 | −5.7 |
| Example 2 Neat Amine | 0.25 | 16.9 | −4.0 |
| Example 2 Neat Amine | 0.5 | 22.1 | 25.6 |
| Comparative Example 3 Neat Amine | 0.1 | 22.6 | 28.4 |
| Comparative Example 3 Neat Amine | 0.25 | 18.5 | 5.1 |
| Comparative Example 3 Neat Amine | 0.5 | 21.6 | 22.7 |

TABLE 1-continued

| Clay Stabilizing Agent | Concentration (% by wt. in water) | 30 Minute Contact Time (sec) | % Change |
|---|---|---|---|
| Example 1 0.5 mol acetate | 0.1 | 17.5 | −0.6 |
| Example 1 0.5 mol acetate | 0.25 | 18.6 | 5.7 |
| Example 1 0.5 mol acetate | 0.5 | 18 | 2.3 |
| Example 2 0.5 mol acetate | 0.1 | 17.3 | −1.7 |
| Example 2 0.5 mol acetate | 0.25 | 16.6 | −5.7 |
| Example 2 0.5 mol acetate | 0.5 | 19.2 | 9.1 |
| Comparative Example 3 0.5 mol acetate | 0.1 | 21 | 19.3 |
| Comparative Example 3 0.5 mol acetate | 0.25 | 18.5 | 5.1 |
| Comparative Example 3 0.5 mol acetate | 0.5 | 20 | 13.6 |
| Comparative Example 4 0.5 mol acetate | 0.1 | 24.2 | 37.5 |
| Comparative Example 4 0.5 mol acetate | 0.25 | 21 | 22.7 |
| Comparative Example 4 0.5 mol acetate | 0.5 | 22.6 | 28.4 |
| Example 1 0.6 mol HCl | 0.1 | 17.7 | 0.6 |
| Example 1 0.6 mol HCl | 0.25 | 17.6 | 0 |
| Example 1 0.6 mol HCl | 0.5 | 17.8 | 1.1 |
| Example 2 0.6 mol HCl | 0.1 | 17.3 | −1.7 |
| Example 2 0.6 mol HCl | 0.25 | 16.5 | −6.3 |
| Example 2 0.6 mol HCl | 0.5 | 16.5 | −6.3 |
| Comparative Example 3 0.6 mol HCl | 0.1 | 21.9 | 24.4 |
| Comparative Example 3 0.6 mol HCl | 0.25 | 18.8 | 6.8 |
| Comparative Example 3 0.6 mol HCl | 0.5 | 18 | 2.3 |
| Example 1 2 mol acetate pH = 6.25 | 0.1 | 19.3 | 9.7 |
| Example 1 2 mol acetate pH = 6.25 | 0.25 | 19.3 | 9.7 |
| Example 1 2 mol acetate pH = 6.25 | 0.5 | 18.3 | 4 |
| Comparative Example 3 2 mol acetate pH = 6.55 | 0.1 | 19.8 | 12.5 |
| Comparative Example 3 2 mol acetate pH = 6.55 | 0.25 | 16.4 | −6.8 |
| Comparative Example 3 2 mol acetate pH = 6.55 | 0.5 | 17 | −3.4 |

Notice the results interpretation. In the CST tests, best clay control chemicals cause less Bentonite swelling; thus, the test solution flows faster through the cup and lower flow times are recorded. Lower numbers (time and % change) indicate better clay control. Negative percent change numbers are obtained when the test solution flows faster than 5% KCl reference solution. Results for tested chemicals (Examples 1 and 2) are generally significant better than results for comparative chemicals (Comparative Examples 3 and 4). Line one in the table illustrates the swelling effect in non-inhibited solution.

Although making and using various embodiments of the present invention have been described in detail above, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

What is claimed is:

1. A water-based well treatment fluid comprising an aqueous continuous phase, a clay stabilizing agent consisting of an alkylated polyetheramine and a weighting material, wherein the alkylated polyetheramine is a compound having a formula (II):

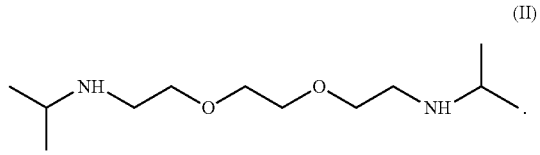 [SMILES: CC(C)NCCOCCOCCNC(C)C]

(II)

2. The water-based well treatment fluid of claim 1, wherein the aqueous continuous phase is selected from fresh water, sea water, brine, a mixture of water and a water soluble organic compound and mixtures thereof.

3. The water-based well treatment fluid of claim 1, wherein the amount of clay stabilizing agent present in the water-based well treatment fluid ranges from about 0.05% to about 0.5% by volume of the water-based well treatment fluid.

4. The water-based well treatment fluid of claim 1, wherein the weighting material is barium sulfate, barite, hematite, iron oxide, calcium carbonate, magnesium carbonate, an organic salt, an inorganic salt or mixtures thereof.

5. The water-based well treatment fluid of claim 1, further comprising one or more additives.

6. A process of making a water-based well treatment fluid comprising admixing a clay stabilizing agent consisting of an alkylated polyetheramine, a weighting material and optional additives with an aqueous continuous phase, wherein the alkylated polyetheramine is a compound having a formula (II):

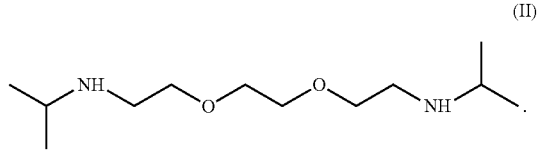 [SMILES: CC(C)NCCOCCOCCNC(C)C]

(II)

7. A water-based well treatment fluid made according to the process of claim 6.

8. A method of inhibiting the swelling and/or migration of clay subterranean materials encountered during the drilling of a subterranean formation comprising circulating in the subterranean formation a water-based well treatment fluid comprising an aqueous continuous phase, a clay stabilizing agent consisting of an alkylated polyetheramine and a weighting material, wherein the alkylated polyetheramine is a compound having a formula (II):

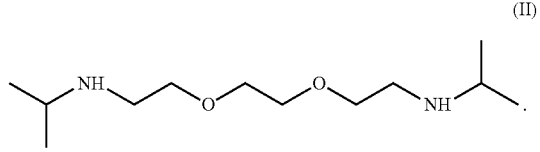 [SMILES: CC(C)NCCOCCOCCNC(C)C]

(II)

9. A method of extracting oil from an oil containing subterranean formation comprising:
providing through a first borehole, a pressurized water-based well treatment fluid comprising an aqueous continuous phase, a clay stabilizing agent consisting of an alkylated polyetheramine and a weighting material, wherein the alkylated polyetheramine is a compound having a formula (II):

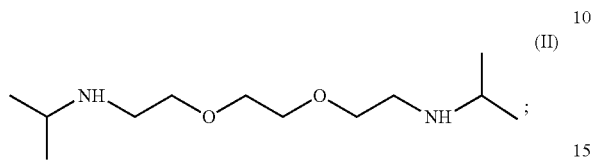

(II)

and
recovering oil from the subterranean formation through a second borehole.

10. The method of claim 9, wherein the subterranean formation was previously hydraulically fractured and oil was previously extracted.

11. The water-based well treatment fluid of claim 1, wherein the weighting material is barium sulfate, barite, hematite, iron oxide, magnesium carbonate, an organic salt, an inorganic salt or mixtures thereof.

12. The water-based well treatment fluid of claim 1, wherein the fluid further comprises at least one of gel breakers, penetration rate enhancers, corrosion inhibitors, lost circulation fluids, anti-bit balling agents, proppants, and sand for gravel packing.

* * * * *